United States Patent
Hacker et al.

(10) Patent No.: US 7,282,128 B2
(45) Date of Patent: Oct. 16, 2007

(54) BUFFERS FOR ELECTROPHORESIS AND USE THEREOF

(75) Inventors: Kevin J. Hacker, San Carlos, CA (US); Karl O. Voss, Foster City, CA (US)

(73) Assignee: Applera Corporation, Foster City, CA (US)

( * ) Notice: Subject to any disclaimer, the term of this patent is extended or adjusted under 35 U.S.C. 154(b) by 511 days.

(21) Appl. No.: 10/198,832

(22) Filed: Jul. 19, 2002

(65) Prior Publication Data

US 2003/0146097 A1 Aug. 7, 2003

Related U.S. Application Data

(63) Continuation-in-part of application No. 09/909,649, filed on Jul. 19, 2001, now abandoned.

(51) Int. Cl.
*G01N 27/447* (2006.01)
*G01N 27/453* (2006.01)

(52) U.S. Cl. ...................... 204/456; 204/606

(58) Field of Classification Search ........ 204/450–462, 204/600–612
See application file for complete search history.

(56) References Cited

U.S. PATENT DOCUMENTS

| | | | |
|---|---|---|---|
| 4,151,043 A | 4/1979 | Bhattacharyya | |
| 4,279,724 A * | 7/1981 | Hearn et al. | 204/610 |
| 4,362,612 A * | 12/1982 | Bier | 204/627 |
| 4,518,608 A | 5/1985 | Kahan | |
| 4,897,169 A * | 1/1990 | Bier et al. | 204/548 |
| 4,936,963 A | 6/1990 | Mandecki et al. | |
| 5,126,021 A | 6/1992 | Grossman | |
| 5,447,612 A | 9/1995 | Bier et al. | |
| 5,552,028 A | 9/1996 | Madabhushi et al. | |
| 5,567,292 A | 10/1996 | Madabhushi et al. | |
| 5,922,185 A | 7/1999 | Updyke et al. | |
| 6,051,636 A * | 4/2000 | Johnson et al. | 524/98 |
| 6,057,106 A | 5/2000 | Updyke et al. | |
| 6,090,252 A | 7/2000 | Bjellqvist | |
| 6,171,463 B1 | 1/2001 | Selby et al. | |
| 6,316,267 B1 | 11/2001 | Bhalgat et al. | |
| 6,387,234 B1 | 5/2002 | Yeung et al. | |
| 6,706,162 B1 * | 3/2004 | Voss et al. | 204/455 |
| 2002/0134680 A1 | 9/2002 | Cabilly et al. | |

FOREIGN PATENT DOCUMENTS

EP 1 074 633 A1 2/2001

(Continued)

OTHER PUBLICATIONS

ACS Registry entry for Bis-Tris.*

(Continued)

*Primary Examiner*—Alex Noguerola
(74) *Attorney, Agent, or Firm*—Knobbe Martens Olson & Bear LLP

(57) ABSTRACT

Various embodiments provide, for example, buffer compositions and/or sieving formulations useful in connection with electrophoresis instruments, such as capillary electrophoresis (CE) devices. In various embodiments, a buffer composition can include Bis-Tris, TAPS and/or TAPSO, and, optionally, a chelating agent, such as EDTA. Methods of separating samples containing bio-molecules, such as DNA or RNA, are also described.

21 Claims, 1 Drawing Sheet

FOREIGN PATENT DOCUMENTS

| WO | 1995/027197 | 10/1995 |
|---|---|---|
| WO | 98/17790 | 6/1998 |
| WO | 99/37813 | 1/1999 |
| WO | 02/24313 | 3/2002 |
| WO | 02/071024 A2 | 9/2002 |

OTHER PUBLICATIONS

Liu et al. ("pK-Matched Running Buffers for Gel Elecrophoresis," Analytical Biochemistry 270, 112-122 (1999)).*

Pages 3-5 to 3-8 of the User Manual for ALFExpress II downloaded from www1.amershambiosciences.com/aptrix/upp00919.nsf/content/1ADB1015B54F1C36C on Feb. 11, 2005.*

Paterson et al. ("Separation of J-Iactoglobulin A, B and C variants of bovine whey using capillary zone electrophoresis," Journa of Chromatography A, 700 (1995) 105-110).*

Buffer pKa/pH Tables and Formulas downloaded from the SigmaAldrich web catalog on Aug. 09, 2006.*

ABI Prism® 3100 Genetic Analyzer User's Manual, Copyright 2001, Applied Biosystems, Section 2, pp. 2-6 to 2-26, Section A, pp. A-3 to A-8.

Novex NuPAGE™ Gel/Buffer Selection Chart, Copyright 2001 Helixx Technologies, Inc., http://www.helixxtec.com/Novex/Consummables/NP-BT.html.

Brush, "Prepare to Cast Off: A Profile of Precast Acrylamide Gels," *The Scientist* 12(15):18 (1998).

Good and Izawa, "Hydrogen Ion Buffers," *Methods in Enzymology vol. XXIV Photosynthesis and Nitrogen Fixation*, Part B, pp. 53-68, Academic Press, New York and London 1972.

Haggie, "Product Review: Novex NuPAGE Bis-Tris Electrophoresis System," *Biocompare—The Buyer's Guide for Life Scientists—Professional Review*, Oct. 3, 2000, University of California, San Francisco.

Lewis, "Mono- and Bis (2-hydroxyethyl) imino-Tris (hydroxymethyl)-methane, 'Mono-tris' and 'Bis-tris': New Buffer Bases with $pK_a^T$ 7.83 and 6.46," *Short Communications*, pp. 495-496, Western Regional Research Laboratory, U.S. Department of Agriculture, Albany, CA, Oct. 22, 1965.

Mills and Kramer, "Structure-Independent Nucleotide Sequence Analysis," *Proc. Natl. Acad. Sci USA*, 76(5):2232-2235 (1979).

Mizusawa et al., "Improvement of the Dideoxy Chain Termination Method of DNA Sequencing by Use of Deoxy-7-deazaguanosine Triphosphate in Place of dGTP," *Nucleic Acids Research*, 14(3):1319-1324 (1986).

Morin, "Creatine Kinase: Re-examination of Optimum Reaction Conditions," *Clinical Chemistry*, 23(9):1569-1575 (1977).

Paabo and Bates, "Dissociation Constant of Protonated 2, 2Bis (dydroxymethyl) -2, 2', 2"-nitrilotriethanol (Bis-tris) and Related Thermodynamic Functions from 0 to 50°," *The Journal of Physical Chemistry*, 74(4):702-705 (1970).

Sanger et al., "DNA Sequencing with Chain-Terminating Inhibitors," *Proc. Natl. Acad. Sci. USA*, 74(12):5463-5467 (1977).

Stellwagen et al., "DNA and Buffers: The Hidden Danger of Complex Formation," *Biopolymers*, 54:137-142 (2000).

Wiltfang et al., "A New Multiphasic Buffer System for Sodium Dodecyl Sulfate-Polyacrylamide Gel Electrophoresis of Proteins and Peptides with Molecular Masses 100 000-1000, and Their Detection with Picomolar Sensitivity," *Electrophoresis*, 12:352-366 (1991).

Search Report from PCT/US02/23039 dated Oct. 11, 2002.

U.S. Appl. No. 60/273,956 filed Mar. 8, 2001.

Voss, Karl O., et al., "The Effective of Temperature Oscillations on DNA Sequencing by Capillary Electrophoresis," *Analytical Chemistry*, vol. 73, No. 6, pp. 1345-1349, Mar. 15, 2001.

He et al. "DNA sequencing with hydrophilic and hydrophobic polymers at elevated column temperatures," Electrophoresis 23, 1421-1428 (2002).

Liang et al., "Formation of concentration gradient and its application to DNA capillary electrophoresis" Electrophoresis, 21, 3600-3608 (2000).

Song, "DNA sequencing by capillary electrophoresis using copolymers of acrylamide and N, N-dimethyl-actylamide," Electrophoresis, 22, 729-736 (2001).

Weber, "Application of binary buffer systems to free flow cell electrophoresis," *Electrophoresis 21*, 325-328 (2000).

* cited by examiner

BUFFERS FOR ELECTROPHORESIS AND USE THEREOF

CROSS REFERENCE TO RELATED APPLICATIONS

This application is a continuation-in-part of U.S. patent application Ser. No. 09/909,649, filed Jul. 19, 2001, abandoned, which is incorporated herein by reference.

FIELD

The present teachings relate to buffer compositions and electrophoresis of biological molecules, such as nucleic acids.

BACKGROUND

Electrophoresis is commonly used to separate biological molecules, such as deoxyribonucleic acid ("DNA"), ribonucleic acid ("RNA"), proteins, etc., according to size or length.

DNA base sequencing and fragment analysis are among the most useful embodiments of electrophoresis separations. In DNA base sequencing, for example, a DNA sequencing product is denatured and the resulting single stranded DNA sample is applied to an electrophoresis gel for separation.

Unfortunately, it is not uncommon to encounter sequencing errors involving specific sequences which are difficult to resolve. One such problem, called a "compression," occurs when the single-stranded fragments anneal to themselves to form a "hairpin" structure at a particular position. The following schematic generally illustrates such an occurrence:

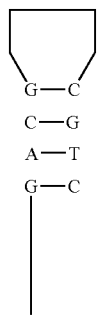

This may cause the fragment to migrate more quickly through the gel than one would expect from its length, which can result in bands that run very close together, sometimes overlapping one another.

SUMMARY

The present teachings provide, among other things, buffer compositions and/or sieving (gel) formulations that improve the performance of electrophoresis instruments, such as capillary electrophoresis (CE) devices.

Various aspects provide a buffer composition for electrophoresis of nucleic acids. The buffer can be, for example, a running buffer.

In various embodiments, the buffer composition includes: (i) Bis-Tris; and (ii) one or more members of the group TAPS, TAPSO, and Asparagine. For example, the composition can comprise Bis-Tris as a cation and TAPS and/or TAPSO as an anion. Various embodiments further include EDTA as a metal chelator.

In various embodiments, the buffer composition includes: (i) TAPS, TAPSO, or Asparagine; and (ii) a compound of the formula: $[HO(CH_2)_m]_3C-N[(CH_2)_n-OH]_2$, wherein: m is an integer of from 1 to 3 (e.g., 1), and n is an integer of from 1 to 4 (e.g., 2).

The composition can include a metal-chelating agent, such as EDTA.

In some embodiments, the composition is substantially free of detergents, such as SDS.

In some embodiments, the composition has a pH greater than 7 (e.g., no less than 7.5). In some embodiments, the composition has a pH less than 8.

In various aspects, the present teachings provide a resolving-gel composition for electrophoresis of nucleic acids.

In various embodiments, the resolving-gel composition includes: (a) an organic polymer, (b) Bis-Tris, and (c) one or more members of the group TAPS, TAPSO, and Asparagine. For example, the composition can comprise Bis-Tris and TAPS and/or TAPSO.

In various embodiments, the composition is substantially detergent-free (e.g., free of SDS).

In some embodiments, the composition has a pH greater than 7 (e.g., no less than 7.5). In various embodiments, the composition has a pH less than 8.

Further aspects of the present teachings relate to apparatus for resolving samples.

In various embodiments, an apparatus includes: an anodic buffer (anolyte) chamber; a cathodic buffer (catholyte) chamber; an electrophoretic channel (e.g., a capillary tube having a lumen) extending between and communicating the anodic and cathodic buffer chambers; and a continuous buffer system comprising Bis-Tris held in the anodic and cathodic buffer chambers and in the channel.

In various embodiments, the continuous buffer system further comprises one or both of TAPS and TAPSO. For example, the buffer system can further comprise TAPS.

In some embodiments, the apparatus further includes a sieving medium (e.g., a gel or flowable (liquid-state) media) held in the channel.

Yet further aspects of the present teachings relate to methods of conducting electrophoresis of nucleic acids.

Various embodiments of such a method comprise: adding a buffer into an electrophoretic channel, wherein the buffer comprises Bis-Tris; adding a sample including nucleic acids to be analyzed into the channel; and resolving the sample by electrophoresis.

Various embodiments of a method of the present teachings comprise: (a) adding a buffer into an electrophoretic channel, wherein the buffer comprises a compound of the formula: $[HO(CH_2)_m]_3C-N[(CH_2)_n-OH]_2$, wherein m is an integer of from 1 to 3 (e.g., 1), and n is an integer of from 1 to 4 (e.g., 2); (b) adding a sample including nucleic acids to be analyzed (e.g., DNA or RNA) into the channel; and (c) resolving the sample by electrophoresis.

In various embodiments, a method of the present teachings comprises: introducing a buffer to a gel, wherein the buffer comprises Bis-Tris; applying a sample including nucleic acids to be analyzed (e.g., DNA or RNA) on the gel; and applying an electromotive potential difference across the gel, whereby the sample is resolved.

In various embodiments, the resolving is carried out at a pH of greater than 7 (e.g., no less than 7.5). In some embodiments, the resolving is carried out a pH of less than 8.

The teachings herein can be particularly useful in connection with channels (e.g., capillary tubes, or grooved plates) having cold zones; e.g., regions of at least 3, 4, 5 cm, or longer, that are not temperature-controlled (e.g., not disposed within a heating apparatus).

DESCRIPTION OF VARIOUS EMBODIMENTS

Figure 1:
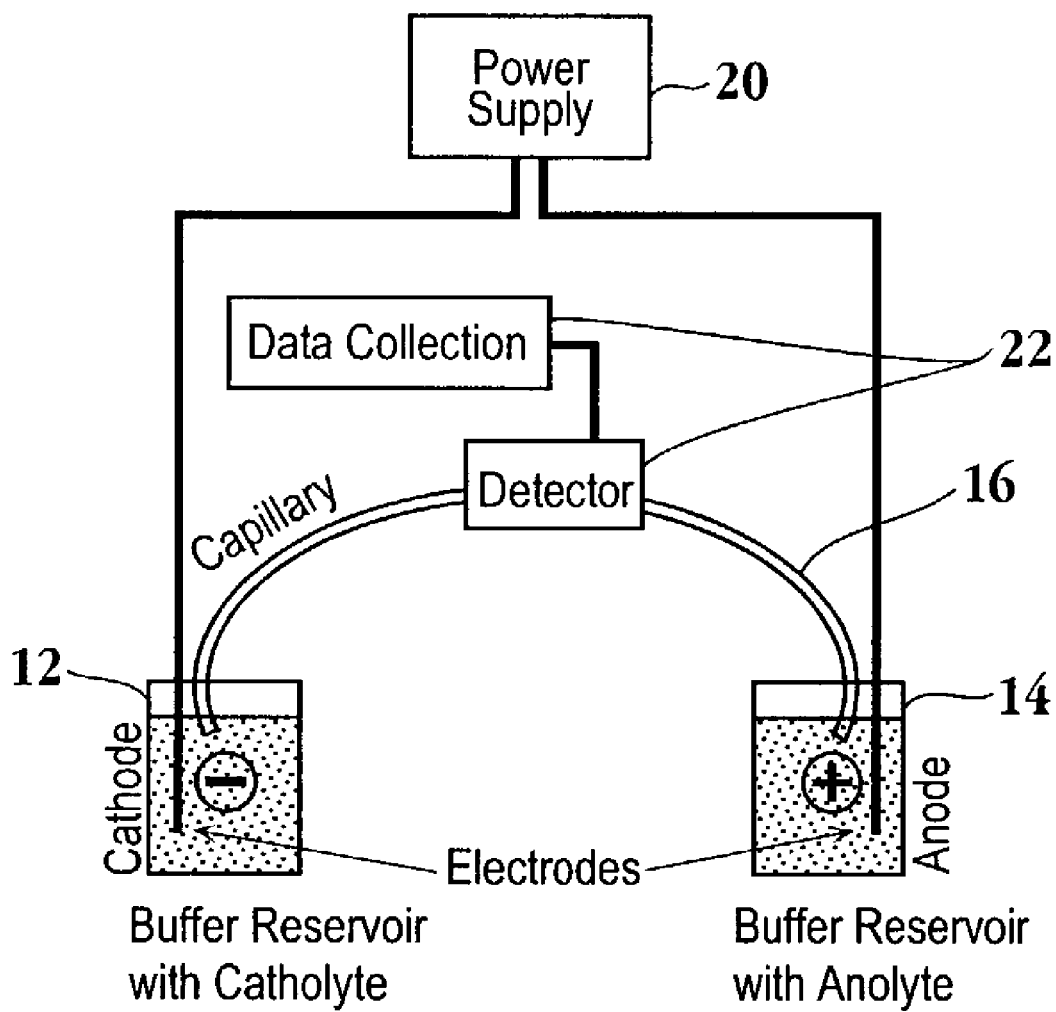
FIG. 1 is a schematic representation of a capillary electrophoresis (CE) device, useful in various embodiments.

Reference will now be made to various non-limiting, exemplary embodiments. It will be understood that such embodiments are not intended to limit the present teachings. On the contrary, the present teachings are intended to cover alternatives, modifications, and equivalents, as will be appreciated by those skilled in the art.

Generally, the present teachings provide, among other things, compositions and methods that facilitate electrophoretic separation (e.g., provide for enhanced resolution).

Embodiments provide, for example, running buffers and/or sieving formulations (e.g., gels or flowable (liquid-state) media) that improve the performance of electrophoresis instruments, such as capillary electrophoresis (CE) devices. The present teachings are not limited, however, to CE devices. In various embodiments, the present teachings provide a composition comprising an electrolyte-containing buffer through which an electric current can be passed.

According to various embodiments, the present teachings provide a buffer for electrophoresis containing a cation configured such that the charge on the cation is hindered (e.g., sterically) from shielding the negative charges on the polynucleotides (e.g., DNA, RNA) of a sample. It has been discovered that such cations can assist in preventing renaturation of denatured DNA. Such effect can be particularly useful in electrophoresis apparatus having regions without means for temperature control, such as a heating assembly. Regions lacking temperature control means are sometimes referred to as "cold zones."

A "cold zone" can be, for example, a region that is at or near ambient temperature during a run. Certain commercial sequencers may have one or more cold zones. For example, in some configurations, an ABI 310 instrument (Applied Biosystems) can include a first cold zone defined by a 6.6 cm region extending from an injection end of the capillary to the instrument's oven, and a second defined by a 3.8 cm region extending from the oven to the detector. In some configurations, an ABI 3100 instrument can include similarly situated cold zones at 4.8 cm and 4.5 cm, respectively. The present teachings can be useful, for example, in connection with such sequencers, among others.

Some embodiments of buffers of the present teachings contain the weak base Bis-Tris (bis[2-Hydroethyl]imino-tris[hydroxymethylmethane) as the cation. In aqueous solution, Bis-Tris molecules pick up protons to give the conjugate acid form, Bis-Tris+.

Bis-Tris is inert, easily prepared, and readily available from commercial sources (see Morin, L. G., Clin. Chem., 23, p. 1569 (1977); and Lewis, J. C., Anal. Biochem. 14, 495 (1966); each of which is incorporated herein by reference). Bis-Tris can be purchased, for example, from Research Organics (Cleveland, Ohio).

In various embodiments, a buffer composition includes (i) Bis-Tris, (ii) TAPS (N-tris[hydroxylmethyl]methyl-3-aminopropane-sulfonic acid), and optionally (iii) a chelating agent. Some formulations provided herein include (i) 100 mM Bis-Tris, (ii) 100 mM TAPS, and (iii) 1 mM EDTA (Ethylenediaminetetraacetic acid, pH 8).

In various embodiments, a buffer composition includes 50–200 mM Bis-Tris (e.g., 100 mM) in a 1:1 ratio with TAPS or TAPSO, and 1–2 mM EDTA. In some embodiments, a buffer comprises 50 mM BisTris, 50 mM TAPSO, and 2 mM EDTA.

In various of the formulations described herein, TAPSO, 3-[N-tris(hydoxymethyl)methylamino]-2-hydroxypropane-sufonic acid, can be substituted for TAPS, or included in addition thereto. Further, Asparagine can be substituted for TAPS in the buffer.

In various embodiments, molecules comprising the following are included in a buffer composition: $[HO(CH_2)_m]_3 C—N[(CH_2)_n—OH]_2$, with m=1, 2, 3, ... m (integral), n (integral), e.g., m=1 to 3 and n=1 to 4, or e.g., m=1 and n=2.

The present teachings provide, in part, gel or flowable separation media compositions for electrophoresis. In various embodiments, a resolving gel composition includes: (a) one or more organic polymers and (b) Bis-Tris. In some embodiments, gel compositions according to the presents teachings further include one or more members of the group TAPS, TAPSO, and Asparagine. In various embodiments, the gel composition includes TAPS and/or TAPSO.

According to various embodiments, a buffer composition is included in a sieving medium (e.g., a gel or flowable separation media); such as the sieving mediums described in U.S. Pat. No. 5,126,021, and WO 02/24313, each of which is incorporated herein by reference.

A composition according to the present teachings can include, for example, a sieving component and a surface interaction component, such as described, for example, in WO 02/24313; incorporated herein by reference.

In various embodiments, the sieving component of the composition contains one or more noncrosslinked acrylamide polymers. Noncrosslinked acrylamide polymers may include, for example, linear polymers such as polyacrylamide (LPA), branched polymers, and star-shaped polymers.

In various embodiments, the surface interaction component of the compositions comprises one or more uncharged and uncrosslinked water-soluble silica-adsorbing polymer. Such compontents may belong to a variety of chemical classes, such as those described in the following references: Molyneux, Water-Soluble Synthetic Polymers: Properties and Behavior, Volumes I and II (CRC Press, Boca Raton, 1982); Davidson, Editor, Handbook of Water-Soluble Gums and Resins (McGraw-Hill, New York, 1980); Franks, editor, Water: A Comprehensive Treatise (Plenum Press, New York, 1973); and the like. The uncharged water-soluble silica-adsorbing polymers of the present teachings can include, but are not limited to, N,N-disubstituted polyacrylamides, N-monosubstituted polyacrylamides, polymethacrylamide, polyvinylpyrrolidone, and the like. In some embodiments, the surface interaction component comprises poly(N,N-dimethylacrylamide) (pDMA).

In various embodiments, polymers of a composition of the present teachings are selected from the group consisting of polyvinylactams, such as polyvinylpyrrolidone; N,N-disubstituted polyacrylamides; and N-substituted polyacrylamides.

Various polymers that can be included in a composition of the present teachings include, but are not limited to, those disclosed in U.S. Pat. No. 5,552,028, U.S. Pat. No. 5,567,292, U.S. Pat. No. 6,387,234; WO 02/24313; H. He et al., *Electrophoresis* 2002, 23 ,1421–1428; and M. N. Albarghouthi et al., Electrophoresis 2001, 22, 737–747; Liguo Song et al., Electrophoresis 2001, 22, 729–736; Dehai Liang et al., Electrophoresis 2000, 21, 3600–3608; each of which is incorporated herein by reference.

Capillary electrophoresis can be performed, for example, using any suitable capillaries, e.g., fused silica capillary tubes, or grooves formed in glass or plastic plates, or in chips. Various embodiments, for example, contemplate the use of elongate tubes, each having an inner diameter, for example, within a range of about 10 to 500 microns, e.g., no greater than about 100 microns. Optionally, each tube can be coated on its outer surfaces along its length with an opaque polyimide coating to prevent breakage. In some embodiments, the separation is performed by filling the capillary tube with only a buffer solution, while in other cases a sieving medium (e.g., polymer or gel) is added, as well. In an exemplary process, a sample is introduced into the inlet end of the capillary tube and an electric field applied. Under the influence of the electric field, the sample separates, causing the individual components to migrate down the length of the capillary tube. At or near the outlet end of the capillary tube, a small region of the opaque polyimide coating can be removed to form an optical detection region. The individual components can be detected using, for example, fluorescence or ultraviolet absorbance.

Details of common features of an operable capillary electrophoresis device may be found in any number of available publications, e.g., *Capillary Electrophoresis Theory and Practice*, Grossman and Colbum, eds., Academic Press (1992), incorporated herein by reference.

According to various embodiments, a buffer in accordance with the present teachings is employed in electrophoretic separations of nucleic acids using a ABI Prism 310 or ABI Prism 3100 sequencing apparatus (Applied Biosystems; Foster City, Calif.).

In various embodiments, a buffer according to the present teachings is employed in a "continuous buffer system." That is, in a system wherein the same buffer of a chosen pH and ionic strength is used in a sieving medium (gel or flowable medium) and in the anode and cathode buffer chambers. FIG. 1, for example, shows a CE device including a cathode buffer reservoir 12, an anode buffer reservoir 14, and a channel defined by a capillary tube 16 extending between the cathode and anode buffer reservoirs. A sieving medium can be held in the channel. A continuous buffer system can be provided by including in both the anode and cathode buffer reservoirs, as well as in the channel, a buffer composition of the present teachings. A sample, loaded into the channel, can be resolved by applying an electromotive potential across the channel by way of an appropriate power source 20. Separated components of the sample can be detected by way of a suitable detection/data-collection assembly 22.

In various embodiments, a Bis-TrisTAPS buffer composition is included in both the cathodic and anodic buffer chambers of a CE apparatus, as well as in a sieving medium (e.g., a resolving gel or flowable medium) held in one or more capillaries of the apparatus. One or more polynucleotide-containing samples can then be resolved using the apparatus, so prepared.

In various embodiments, separation of a nucleic acid-containing sample is effected at a pH of at least 7, of greater than 7, and/or at least 7.5. In some embodiments, separation is effected at a pH of 8, or less.

The following examples are intended for illustration purposes only, and should not be construed as limiting in any way.

EXAMPLE 1

A buffer solution in accordance with the present teachings was formulated as: 100 mM Bis-Tris (bis[2-Hydroethyl] imino-tris[hydroxymethylmethane), 100 mM TAPS (N-tris [hydroxylmethyl]methyl-3-aminopropane-sulfonic acid), and 1 mM EDTA (Ethylenediaminetetraacetic acid, pH 8).

1 mM EDTA was used to eliminate or alleviate damage to the capillary coating due to metals.

EXAMPLE 2

Less temperature induced DNA band broadening was observed with TrisTAPS than with NaTAPS (Tris-(hydroxymethyl)-methyl-amino-propanesulfonic acid, sodium salt) running buffer. To understand how the cations, Tris and Na, influence DNA band broadening during electrophoresis, DNA separation and mobility were examined during capillary electrophoresis with running buffers containing the different metal cations: Li, Rb, Ca, Mg, K, and Cs; and organic buffers, Bis-Tris, TrisBispropane, imidizole, arginine, ammonium, and tetrapentylammonium. It was noticed that the sizing of a fragment, referred to herein as GS700 250 nucleotide (nt) fragment, or simply the 250 nt fragment, which has putative DNA secondary structure that causes it to run anomalously under low DNA denaturant conditions, was running near its predicated size (250 nt) with Bis-TrisTAPS as the running buffer during capillary electrophoresis. From an examination of the structure of the Bis-Tris molecule, it is believed that Bis-Tris may be sterically hindered from shielding the negative ions on the DNA backbone, thereby-reducing its ability to renature during electrophoresis.

EXAMPLE 3

The ability of the buffer of the present teachings to improve nucleic acid denaturation during electrophoresis was observed in the following assays:

EXAMPLE 3(A)

One assay measured the ability of the present buffer to reduce the anomalous mobility of the GS700 250 nucleotide (nt) fragment—the anomalous mobility is thought to be due to DNA secondary structure. The results from this assay are reported in Table I. During electrophoresis at 70° C. on the ABI Prism 310 instrument using POP37 polymer (Applied Biosystems; Foster City, Calif.), with TrisTAPS as the running buffer, the 250 nt fragment migrated as 244.5 nt, and with an additional 1 M urea in the polymer formulation, the 250 nt fragment migrated as 245.5 nt. Using Bis-Tris buffer (without additional urea) the 250 nt fragment migrated as a 247.5 nt fragment—closer to the correct 250 nt than obtained by adding an additional 1 M urea to the polymer.

TABLE I

| | Migration of the 250 nt fragment | | |
|---|---|---|---|
| buffer cation | 50° C. | 60° C. | 70° C. |
| Na | 241.7 | ND | 244.9 |
| Tris | 242.7 | ND | 244.5 |
| Tris + 1 M urea* | 244.8 | 244.7 | 245.5 |
| Bis-Tris | 246.0 | 247.0 | 247.4 |

*additional urea added to polymer formulation

EXAMPLE 3(B)

Second, the ability to reduce the severity of a 4 base compression, CGCC, was measured. The spacing of the C terminated fragments flanking the compression were measured and then the deviation of the C nucleotides in the compression from the normal spacing was calculated. Completely normal spacing or no compression would result in "0" deviation. The less the DNA is denatured, the greater compression, and, therefore, the larger the deviation of the 3 C nucleotides from normal. Table II shows the smallest deviation with Bis-Tris buffer, and once again more denaturation is seen with the switch to Bis-Tris buffer than with the addition of an extra 1 M urea.

TABLE II

| buffer cation | temp. (° C.) | C base | scan # | y-inter | slope | cal base | difference | sum dev. |
|---|---|---|---|---|---|---|---|---|
| Bis-Tris | 60 | 10 | 3123 | 3011.4 | 10.5 | 10.62857 | 0.628571 | |
| | | 12 | 3131 | 3011.4 | 10.5 | 11.39048 | 0.609524 | |
| | | 13 | 3131 | 3011.4 | 10.5 | 11.39048 | 1.609524 | 2.847619 |
| | 65 | 10 | 3006 | 2898.8 | 10.31 | 10.39767 | 0.397672 | |
| | | 12 | 3016 | 2898.8 | 10.31 | 11.3676 | 0.632396 | |
| | | 13 | 3016 | 2898.8 | 10.31 | 11.3676 | 1.632396 | 2.662464 |
| | 70 | 10 | 2999 | 2888.8 | 10.57 | 10.42573 | 0.425733 | |
| | | 12 | 3010 | 2888.8 | 10.57 | 11.46641 | 0.533586 | |
| | | 13 | 3010 | 2888.8 | 10.57 | 11.46641 | 1.533586 | 2.492904 |
| Tris | 60 | 10 | 3502 | 3394 | 9.76 | 11.06557 | 1.065574 | |
| | | 12 | 3502 | 3394 | 9.76 | 11.06557 | 0.934426 | |
| | | 13 | 3502 | 3394 | 9.76 | 11.06557 | 1.934426 | 3.934426 |
| | 65 | 10 | 3338 | 3231.3 | 9.54 | 11.18449 | 1.184486 | |
| | | 12 | 3338 | 3231.3 | 9.54 | 11.18449 | 0.815514 | |
| | | 13 | 3338 | 3231.3 | 9.54 | 11.18449 | 1.815514 | 3.815514 |
| | 70 | 10 | 3151 | 3047.3 | 9.22 | 11.24729 | 1.247289 | |
| | | 12 | 3151 | 3047.3 | 9.22 | 11.24729 | 0.752711 | |
| | | 13 | 3151 | 3047.3 | 9.22 | 11.24729 | 1.752711 | 3.752711 |
| Na | 60 | 10 | 3487 | 3377.6 | 10.02 | 10.91816 | 0.918164 | |
| | | 12 | 3487 | 3377.6 | 10.02 | 10.91816 | 1.081836 | |
| | | 13 | 3487 | 3377.6 | 10.02 | 10.91816 | 2.081836 | 4.081836 |
| | 65 | 10 | 3408 | 3292.4 | 10.315 | 11.20698 | 1.20698 | |
| | | 12 | 3408 | 3292.4 | 10.315 | 11.20698 | 0.79302 | |
| | | 13 | 3408 | 3292.4 | 10.315 | 11.20698 | 1.79302 | 3.79302 |
| | 70 | 10 | 3338 | 3223.8 | 10.154 | 11.2468 | 1.246799 | |
| | | 12 | 3338 | 3223.8 | 10.154 | 11.2468 | 0.753201 | |
| | | 13 | 3338 | 3223.8 | 10.154 | 11.2468 | 1.753201 | 13.753201 |
| Tris + 1 M urea* | 60 | 10 | 4191 | 4067.7 | 11.01 | 11.19891 | 1.19891 | |
| | | 12 | 4191 | 4067.7 | 11.01 | 11.19891 | 0.80109 | |
| | | 13 | 4191 | 4067.7 | 11.01 | 11.19891 | 1.80109 | 3.80109 |
| | 65 | 10 | 3968 | 3846.9 | 10.655 | 11.36556 | 1.365556 | |
| | | 12 | 3968 | 3846.9 | 10.655 | 11.36556 | 0.634444 | |
| | | 13 | 3968 | 3846.9 | 10.655 | 11.36556 | 1.634444 | 3.634444 |
| | 70 | 10 | 3730 | 3625 | 9.8 | 10.71429 | 0.714286 | |
| | | 12 | 3735 | 3625 | 9.8 | 11.22449 | 0.77551 | |
| | | 13 | 3735 | 3625 | 9.8 | 11.22449 | 1.77551 | 3.265306 |

*The polymer was formulated with an additional 1 M urea.

It will be appreciated that various embodiments of the present teachings provide running buffers useful, for example, in capillary electrophoresis of DNA, especially when increased DNA denaturation is desired. Embodiments of the present teachings can provide for increased DNA denaturation during electrophoresis, without significant loss of DNA resolution or run speed, which is commonly observed with extra chemical denaturants such as urea or 2-pyrrolidinone.

Optionally, the compositions and methods described herein can be employed in combination with other methods aimed at alleviating or minimizing compressions. For example, one method involves sequencing of the other strand, as the factors contributing to the secondary structure are often not found on the complementary strand. Another strategy to eliminate compressions is to include organic solvents such as formamide and/or urea in the gel in an attempt to reduce the amount of base pairing. Yet a further strategy is to lower the stability of the secondary structures in the product strand by substituting ITP or 7-deaza-dGTP for GTP. Also, heat can be used in to disrupt hydrogen bonds, resulting in denatured DNA and RNA.

Although the present teachings have been described with reference to various applications, methods, and compositions, it will be appreciated that various changes and modifications may be made without departing from the spirit hereof. The foregoing examples are provided to further illustrate the present teachings and are not intended as limiting.

The invention claimed is:

1. A buffer composition for electrophoresis of nucleic acids, the buffer composition comprising:
   (i) Bis-Tris
   (ii) TAPS; and
   (iii) a metal-chelating agent, wherein the pH of the buffer is no less than 7.5.

2. The composition of claim 1, wherein said metal-chelating agent includes EDTA.

3. The composition of claim 2, wherein the composition is substantially detergent-free.

4. The composition of claim 1, wherein the composition is substantially detergent-free.

5. A buffer composition for electrophoresis of nucleic acids, the buffer composition comprising:
(i) at least one of TAPS, TAPSO, and Asparagine; and
(ii) a compound of the formula: $[HO(CH_2)_m]_3C-N[(CH_2)_{n-OH}]_2$,
wherein: m is an integer of from 1 to 3, and n is an integer of from 1 to 4; and further comprising a metal-chelating agent, and wherein the buffer composition has a pH of no less than 7.5.

6. The composition of claim 5, wherein said metal-chelating agent is EDTA.

7. The composition of claim 5, wherein the composition is substantially detergent-free.

8. The buffer composition of claim 5 comprising TAPS.

9. The buffer composition of claim 5 comprising TAPSO.

10. The buffer composition of claim 5 comprising Asparagine.

11. A resolving-gel composition for electrophoresis of nucleic acids, the composition comprising:
(a) an organic polymer,
(b) Bis-Tris,
(c) one or more members of the group TAPS, TAPSO, and Asparagine; and
(d) a metal-chelating agent,
wherein the organic polymer comprises a sieving component comprising a non-crosslinked acrylamide polymer, and a surface interaction component comprising one or more non-crosslinked polymers selected from the group consisting of N,N-disubstituted polyacrylamide and N-substituted polyacrylamide, and wherein the resolving-gel composition has a pH of no less than 7.5.

12. The composition of claim 11, having a pH greater than 7.

13. The composition of claim 11, comprising TAPSO.

14. The composition of claim 11 comprising Asparagine.

15. An apparatus for resolving samples, comprising:
an anodic buffer chamber;
a cathodic buffer chamber;
an electrophoretic channel extending between and communicating said anodic and cathodic buffer chambers; and
a continuous buffer system comprising Bis-Tris held in said anodic and cathodic buffer chambers and in said channel;
wherein said continuous buffer system further comprises one or both of TAPS and TAPSO, and wherein said continuous buffer system has a pH of no less than 7.5.

16. The apparatus of claim 15, further comprising a sieving medium held in said channel.

17. The apparatus of claim 15, further comprising an organic polymer, wherein the organic polymer comprises a sieving component comprising a non-crosslinked acrylamide polymer, and a surface interaction component comprising one or more non-crosslinked polymers selected from the group consisting of N,N-disubstituted polyacrylamide and N-substituted polyacrylamide.

18. A method of electrophoresis of nucleic acids, comprising:
adding a buffer into an electrophoretic channel, wherein said buffer comprises Bis-Tris, TAPS and a metal-chelating agent, and wherein said buffer has a pH of no less than 7.5;
adding a sample including nucleic acids to be analyzed into said channel; and
resolving said sample by electrophoresis, wherein said channel is defined by a capillary tube.

19. A method of electrophoresis of nucleic acids, comprising:
(a) adding a buffer into an electrophoretic channel, wherein said buffer comprises a compound of the formula: $[HO(CH_2)m]_3C-N[(CH_2)_{n-OH}]_2$,
wherein m is an integer of from 1 to 3, and n is an integer of from 1 to 4, and
wherein the buffer further comprises TAPS or TAPSO and a metal-chelating agent;
(b) adding a sample including nucleic acids to be analyzed into said channel; and
(c) resolving said sample by electrophoresis, at a pH of no less than 7.5,
wherein said channel is defined by a capillary tube, and wherein at least a portion of the gel is at an ambient temperature during the application of the electromotive potential difference across the gel.

20. The method of claim 19, wherein the metal-chelating agent is EDTA.

21. The method of claim 19, wherein the buffer includes TAPS.

* * * * *